US010744268B2

(12) United States Patent
McCann et al.

(10) Patent No.: US 10,744,268 B2
(45) Date of Patent: Aug. 18, 2020

(54) SYRINGE PLUNGER SYSTEM WITH SELF-LOCKING THREADED GEOMETRY

(71) Applicant: TOLMAR THERAPEUTICS, INC., Fort Collins, CO (US)

(72) Inventors: Kevin McCann, Fort Collins, CO (US); Eric Mugoye, Fort Collins, CO (US); Dominic Madril, Loveland, CO (US)

(73) Assignee: TOLMAR THERAPEUTICS, INC., Fort Collins, CO (US)

( * ) Notice: Subject to any disclaimer, the term of this patent is extended or adjusted under 35 U.S.C. 154(b) by 48 days.

(21) Appl. No.: 15/526,410

(22) PCT Filed: Dec. 4, 2015

(86) PCT No.: PCT/US2015/063934
§ 371 (c)(1),
(2) Date: May 12, 2017

(87) PCT Pub. No.: WO2016/090220
PCT Pub. Date: Jun. 9, 2016

(65) Prior Publication Data
US 2017/0326300 A1 Nov. 16, 2017

Related U.S. Application Data

(60) Provisional application No. 62/087,436, filed on Dec. 4, 2014.

(51) Int. Cl.
*A61M 5/315* (2006.01)
*F16B 39/30* (2006.01)

(52) U.S. Cl.
CPC .... *A61M 5/31515* (2013.01); *A61M 5/31511* (2013.01); *F16B 39/30* (2013.01); *A61M 2205/19* (2013.01)

(58) Field of Classification Search
CPC . A61M 5/31511; A61M 5/31515; F16B 39/30
See application file for complete search history.

(56) References Cited

U.S. PATENT DOCUMENTS 5,875,976 A * 3/1999 Nelson .................... A61M 5/30
239/329
6,645,177 B1   11/2003 Shearn
(Continued)

FOREIGN PATENT DOCUMENTS

DE          3920678      1/1991
GE         201706798    12/2017
(Continued)

OTHER PUBLICATIONS

Translation of JP2012135664 courtesy of the Global Dossier file record for that application. (Year: 2012).*
(Continued)

*Primary Examiner* — Phillip A Gray
(74) *Attorney, Agent, or Firm* — Sheridan Ross P.C.

(57) ABSTRACT

A plunger rod system for syringes is provided. The system comprises at least one plunger and an associated rod for imparting force to the plunger. The rod comprises an end with a threaded member, and the threaded member comprises threads of a certain geometry that enable ease of installation of the rod within the plunger while also providing resistance to pull-out forces such as may be imparted when pulling or extracting the rod or plunger from a barrel.

19 Claims, 5 Drawing Sheets

FIG.2

(56) References Cited

U.S. PATENT DOCUMENTS

| | | | |
|---|---|---|---|
| 7,645,267 B2 | 1/2010 | Vetter et al. | |
| 7,850,211 B2* | 12/2010 | Reynolds, Jr. | F16L 15/004 |
| | | | 285/334 |
| 8,002,754 B2 | 8/2011 | Kawamura et al. | |
| 2004/0009609 A1* | 1/2004 | Yarborough | A61M 5/002 |
| | | | 436/174 |
| 2011/0028913 A1 | 2/2011 | Muramatsu et al. | |
| 2011/0303703 A1* | 12/2011 | Yeager | A61M 5/282 |
| | | | 222/386 |
| 2012/0016314 A1* | 1/2012 | Tachikawa | A61M 5/31515 |
| | | | 604/222 |

FOREIGN PATENT DOCUMENTS

| | | |
|---|---|---|
| JP | H09-308689 | 12/1997 |
| JP | 2009-165524 | 7/2009 |
| JP | 2012-135664 | 7/2012 |
| JP | 2013-070788 | 4/2013 |
| WO | WO 2014/155114 | 10/2014 |

OTHER PUBLICATIONS

Official Action for European Patent Application No. 15813216.7, dated Apr. 16, 2018 4 pages.

International Search Report and Written Opinion for International (PCT) Patent Application No. PCT/US2015/063934, dated Apr. 28, 2016 12 pages.

International Preliminary Report on Patentability for International (PCT) Patent Application No. PCT/US2015/063934, dated Jun. 15, 2017 8 pages.

Intention to Grant for European Patent Application No. 15813216.7, dated Oct. 2, 2018 8 pages.

Official Action with English Translation for Georgia Patent Application No. 14523/01, dated Mar. 6, 2019 11 pages.

Official Action with English Translation for Eurasia Patent Application No. 2017/00270, dated Aug. 27, 2018 3 pages.

* cited by examiner

SYRINGE PLUNGER SYSTEM WITH SELF-LOCKING THREADED GEOMETRY

CROSS REFERENCE TO RELATED APPLICATIONS

This application is a national stage application under 35 U.S.C. 371 of PCT Application No. PCT/US2015/063934, having an international filing date of Dec. 4, 2015, which designated the United States, which PCT application claimed the benefit of U.S. Application Ser. No. 62/087,436, filed Dec. 4, 2014, both of which are incorporated by reference in their entirety.

FIELD OF THE INVENTION

Embodiments of the present invention relate to syringe plunger and plunger rod systems. More specifically, embodiments of the present invention provide self-locking syringe plungers and rods that provide enhanced pull-out resistance between a rod and a plunger or stopper.

BACKGROUND

U.S. Pat. No. 6,645,177 to Shearn, which is incorporated herein by reference in its entirety, discloses a syringe driver system with a threaded lead screw shaft and a plunger. The threaded features of Shearn relate to controlled dosing of a substance from the syringe. Shearn fails to provide a threaded shaft or plunger assembly with enhanced pull out resistance.

U.S. Pat. No. 7,645,267 to Vetter et al., which is incorporated herein by reference in its entirety, provides a prefilled syringe with a plunger provided in the barrel and a thread system cooperating with the plunger rod and the finger support. The thread system of Vetter et al., however, fails to disclose various locking and enhanced pull out features.

U.S. Pat. No. 8,002,754 to Kawamura et al., which is incorporated herein by reference in its entirety, provides a plunger rod with a threaded portion to permit attachment between the rod and a piston. Kawamura et al. fails to disclose, however, locking features associated with the threaded portion to secure the threaded portion and a stopper or piston.

SUMMARY

In one embodiment of the present invention, a plunger rod useful for supporting and sliding a stopper in a syringe barrel is provided, the plunger rod having a threaded portion formed at an end of said plunger rod to attach the stopper on the plunger rod and a flange formed at an opposite end of the plunger rod. In certain embodiments, the threaded portion comprises at least one of a barb, a spur, and a projection departing from a general path of a pitch of the threaded portion.

In one embodiment of the present invention, a syringe is provided, the syringe comprising a barrel provided at an end thereof with a medicament delivery tip sealed with a closure and is open at an opposite end thereof, and a piston having a screw bore formed along a central axis of the piston in a rear portion of the piston and slidably sealing the open end of said syringe barrel. In certain embodiments, the syringe further comprises a plunger rod with a threaded portion as shown and described herein.

A long felt need for an effective system for securing a plunger and a plunger rod for syringes, including prefilled syringes, exists. In particular, a system that provides quick and easy assembly of syringe components, while still providing adequate pull-out resistance is required. Accordingly, embodiments of the present invention provide a syringe with a plunger rod wherein the plunger rod comprises a threaded portion. The threaded portion further comprises at least one securing feature to increase the pull out or other removal resistance of rod-stopper combination. In preferred embodiments, the securing features of the threaded portion allow the rod to be inserted and connected in a relatively easy manner, while still providing an improved fit between the items.

In various embodiments, the invention allows for components with a "self-locking" male thread geometry to be attached to a component with similar female thread geometry. Mating of such components allow for the "self-locking" features to function in providing mechanical resistance when any attempt to unscrew/detach the male component from the female component occurs and/or when the plunger is pulled or extracted from the syringe barrel. The thread geometry consists of the thread pitch, thread count, thread angle, and thread "self-locking" features. The thread angle is the angle of an individual thread as measured from a thread trough to an outer thread surface when compared to a perpendicular extending from longitudinal axis. Thread count is the number of threads per unit of longitudinal measure (e.g. "threads per inch"). "Pitch" is the distance from one thread to the next as measured along the length of the axis.

Plunger rod systems with locking features as shown and described herein may be employed in various different plunger and syringe systems. Although various embodiments of the present invention contemplate a plunger rod assembly with a locking thread pattern for use with a mixing syringe, wherein a plunger rod and associated stopper are provided to seal an open end of a syringe barrel and be removed prior to mixing or use of the device, locking thread features as provided herein may be provided in combination with any number of syringes. One example of a mixing syringe system that may be provided with features of the present invention as shown and described herein is a mixing syringe system for ELIGARD® (leuprolide acetate for injectable suspension). In certain embodiments, a plunger rod with self-locking threads comprises features for preventing translation of the rod and/or stopper beyond a certain point within the barrel. In alternative embodiments, however, it is contemplated that locking thread features may be provided on any number or type of syringe plunger(s), including syringe plungers provided as working plungers that are adapted to connect to a stopper and translate the stopper along the entirety of the syringe barrel length, or at least a majority thereof.

In one embodiment, a plunger rod useful for supporting and sliding a stopper in a syringe barrel is provided. The plunger rod comprises a first end and a second end, where the first end has a user-interface portion with a flange. The second end comprises a threaded portion adapted for interconnection to at least one of a plunger and a stopper. The threaded portion comprises a shaft having an external male thread and a predetermined thread geometry. The external male thread comprises a locking element, wherein the locking element comprises at least one of a barb, a spur, and a projection departing from a general path of a pitch of the threaded portion, and wherein the external male thread provides enhanced pull-out resistance of the at least one of a plunger and a stopper.

In another embodiment, a plunger rod useful for supporting and sliding a stopper in a syringe barrel is provided wherein the plunger rod comprises a first end and a second end. The first end comprises a user-interface portion and the second end comprises a threaded portion adapted for interconnection to at least one of a plunger and a stopper. The threaded portion comprises an external male thread and a predetermined thread geometry having a first thread angle. The external male thread comprises a locking element, wherein the locking element comprises at least one projection departing from a general path of a pitch of the threaded portion, the projection comprising a second thread angle and a point and wherein the second thread angle is greater than the first thread angle. The external male thread provides enhanced pull-out resistance of the at least one of a plunger and a stopper.

In yet another embodiment, a syringe including a barrel, a plunger rod, and stopper is provided. The plunger comprises a first end and a second end and the first end comprising a user-interface portion. The second end comprises a threaded portion adapted for interconnection to at least one of a plunger and a stopper. The threaded portion comprises an external male thread and a predetermined thread geometry having a first thread angle. The external male thread comprises a locking element with at least one projection departing from a general path of a pitch of the threaded portion, the projection comprising a second thread angle and a point and wherein the second thread angle is greater than the first thread angle. The locking element extends at least partially into the at least one of a plunger and a stopper and the plunger rod provides enhanced removal or pull-out resistance of the at least one of a plunger and a stopper. In various embodiments, the locking element comprises a barb, and the male threaded portion comprises a thread angle of between approximately 5.0 and 10.0 degrees, and preferably of about 7.0 and 8.0 degrees and the barb comprises a thread angle of between approximately 15.0 and 25.0 degrees. In various embodiments, the locking element comprises a thread angle of between approximately 18.0 and 20.0 degrees. In various embodiments, an external male thread member comprises at least 15 threads per inch. The male threaded portion may comprise a thread pitch of between approximately 0.050 inches and 0.075 inches.

In various embodiments, a plunger rod is integrally formed with at least one resin selected from the group consisting of cyclic olefin resins, radiation-resistant polypropylenes, polypropylene, polycarbonates and polystyrene. The plunger rod may comprise any suitable length, and preferably comprises a length of between approximately 0.50 inches and 1.00 inches. The plunger rod may be fitted with at least one of a plunger and a stopper provided in force-transmitting communication with the external male thread. The plunger rod of claim 13, wherein the plunger rod and the at least one of a plunger and a stopper are provided in combination with a syringe having a barrel, and wherein the plunger rod and the at least one of a plunger and a stopper comprise selectively removable elements.

The Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

BRIEF DESCRIPTION OF THE DRAWINGS

The drawings constitute a part of this specification and include exemplary embodiments of the present invention and illustrate various objects and features thereof.

DETAILED DESCRIPTION OF THE INVENTION

It is to be understood that while certain forms of the present invention have been illustrated and described herein, it is not to be limited to the specific forms or arrangement of parts described and shown.

Figure 1:
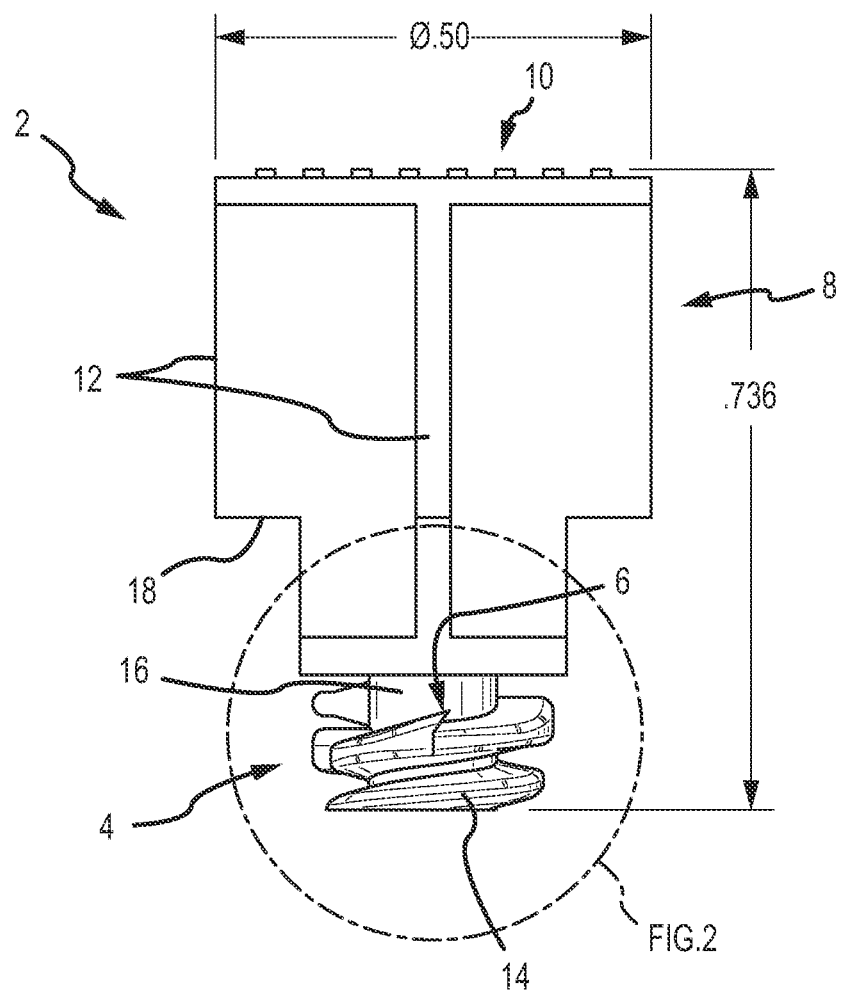
FIG. 1 is a front elevation view of a plunger according to one embodiment of the present invention.

As shown in FIG. 1, a plunger rod assembly 2 according to one embodiment of the present invention is provided. The plunger rod assembly 2 comprises a first end having a threaded portion 4. The threaded portion 4 comprises a male threaded member for interconnection to a piston or stopper (not shown in FIG. 1). The threaded portion 4 comprises external threads. At least one locking element 6 is provided on at least one external thread. In various embodiments, the locking element 6 comprises a barb or projection, wherein the locking element 6 comprises a departure from the general path or pitch of the threads. The projection preferably comprises a second thread geometry that is different from a thread geometry of the threaded portion and that comprises a point 7 (see FIG. 2). For example, in one embodiment, the projection enables the locking element to extend at least partially into at least one of a plunger and a stopper, such that the plunger rod provides enhanced pull-out resistance of the plunger and/or stopper. In various embodiments, a threaded portion of the present invention comprises a thread pitch of approximately 0.0625 inches, and/or comprises about 16 threads per inch. The locking element 6 comprises a self-locking feature for securing the plunger rod assembly 2 with a corresponding element, such as a stopper or piston. In various embodiments, the assembly 2 is adapted for connection with a rubber stopper comprising a female aperture or bore. The locking element 6 comprises a barb capable of engaging the stopper. Specifically, the threaded portion of the embodiment of FIG. 1 comprises right-handed threads adapted to be inserted or threaded into a plunger with a clockwise rotation. Removal of the plunger rod assembly 2 from the stopper, through counter-clockwise rotation and/or application of tension force on the assembly 2, is inhibited by the geometry of the locking element 6. Insertion of the plunger rod assembly 2, however, is not substantially inhibited and the plunger rod assembly 2 may be inserted into a piston or stopper without the need for accessing force, additional tooling, etc.

As further shown in FIG. 1, the plunger rod assembly 2 comprises a shaft portion 8 that extends between the first end with the threaded portion 4 and a second end comprising a user-interface portion 10. The user-interface portion 10 of the depicted embodiment comprises a substantially planar portion adapted for contact with a user's thumb (for example) for depression of the plunger rod assembly and activation of the device (e.g. prefilled syringe). In the depicted embodiment, the shaft portion 8 comprises a plurality of ribs 12 provided at right angles to one another. The ribs 12 provide structural support to the plunger rod and shaft portion 8, while reducing the overall volume and weight of the shaft portion 8.

As shown in FIG. 1, the plunger rod assembly 2 comprises an overall length of between approximately 0.50 inches and 1.00 inches. In preferred embodiments, the overall length of the plunger rod assembly 2 is between approximately 0.70 inches and 0.80 inches. In a preferred embodiment, the length of the plunger rod assembly 2 is approximately 0.736 inches. In the depicted embodiment, the plunger rod 2 comprises a relatively short overall length as it is not designed for dispensation of contents from a syringe. Rather, the rod 2 of shaft portion 8 of the depicted embodiment is designed to secure a stopper at a distal end of a syringe barrel to seal or close the barrel and maintain a sterile object including, but not limited to, a sterile injectable solution or suspension. Prior to use of the syringe device, the plunger rod assembly 2 including the shaft portion 8, the threaded portion 4 and any associated stopper is extracted from the barrel and typically discarded. In the depicted embodiment, and in various embodiments wherein the plunger rod and associated plunger or stopper are designed to seal or enclose a syringe barrel and ultimately intended to be extracted, it will be recognized that the pull-out resistance of the plunger rod with respect to the plunger or stopper is critical. In such embodiments, and in embodiments wherein the plunger comprises a mixing syringe wherein a tension is intended to be applied to the plunger on at least one occasion and the plunger rod is provided to withstand and tolerate more than a compression force, embodiments of the present disclosure provide an improved connection between the plunger rod and the plunger. The improved connection eliminates or reduces the risk that the plunger rod will be accidentally withdrawn from the plunger, leaving the plunger stuck in the barrel and the device generally rendered useless.

In various embodiments, a user-interface portion 10 comprises a substantially circular element with a diameter of between approximately 0.25 inches and 0.75 inches. In a preferred embodiment, the diameter of the user interface portion 10 is approximately 0.50 inches.

Figure 2:
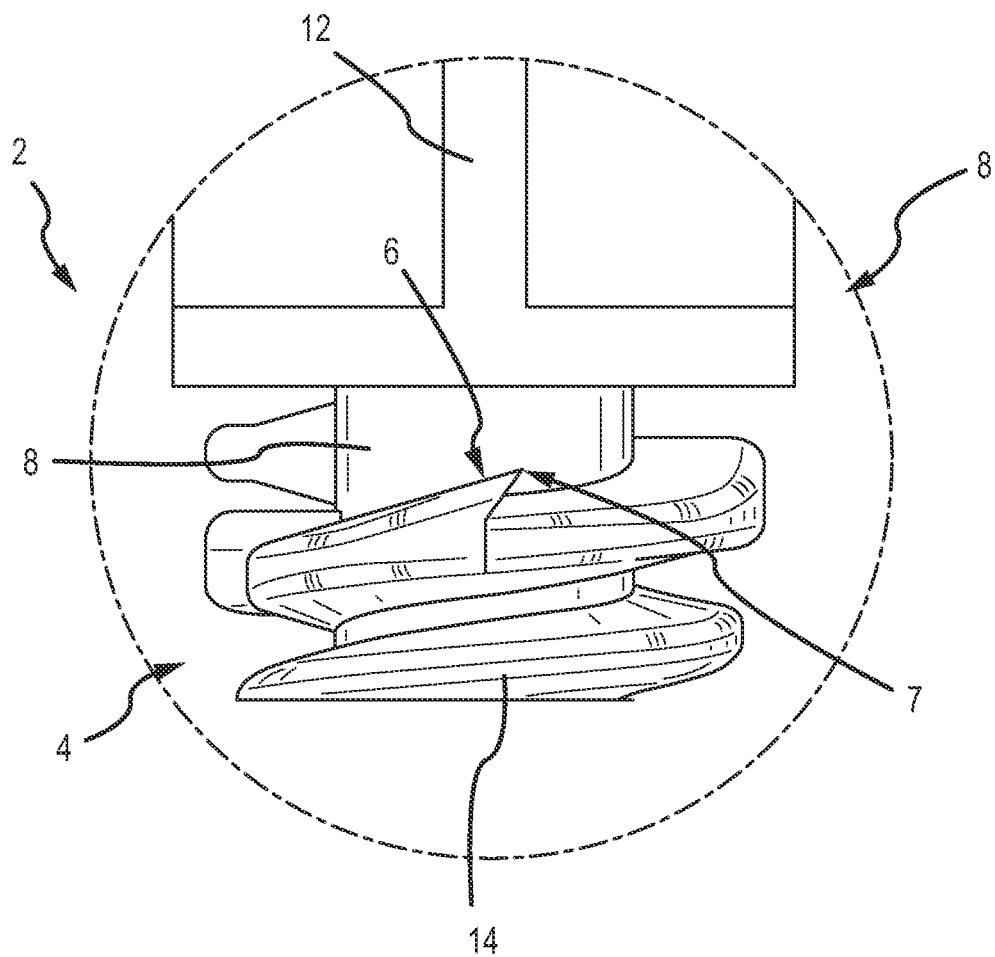
FIG. 2 is a detailed front elevation view of the plunger according to FIG. 1 and taken about detail 2.

FIG. 2 is a detailed side elevation view of the embodiment of FIG. 1 and taken about detail 2 of the FIG. 1. As shown, the threaded portion 4 comprises a locking element 6, wherein the locking element 6 comprises a projection 7 deviating from the external thread(s) 14. In certain embodiments, the external threads 14 comprise a thread pitch of between approximately 0.025 inches and 0.075 inches, and the locking element 6 comprises a thread angle of between 15.0 and 25.0 degrees. In one embodiment, the external threads 14 comprise a thread pitch of between approximately 0.050 inches and 0.075 inches. In a preferred embodiment, the threaded portion 4 comprises external threads 14 having pitch of approximately 0.062 inches, and a locking element 6 comprises a barb or projection extending from the external threads with a thread angle that is greater than a thread angle of the external threads 14, and between approximately 18.0 and 20.0 degrees. In various embodiments, a thread angle of the external threads is approximately 7.20 degrees, and the thread angle of the locking element 6 is approximately 18.8.

In the embodiment provided in FIG. 2, the external threads 14 are provided on a cylinder portion 8. Although certain embodiments of the present invention are shown and described herein, it will be recognized that the geometries, pitches, and thread angles of certain embodiments are not to be viewed as limiting. Indeed, any number of variations to these dimensions and geometries may be provided without diverging from the scope and spirit of the present invention. Although various thread geometries, including those described above, are described herein, it will be recognized that the present disclosure is not limited to a particular thread geometry. However, a plunger rod with a shaft having a threaded portion with an external male thread and a predetermined thread geometry as shown and described herein is contemplated by various preferred embodiments.

Figure 3:
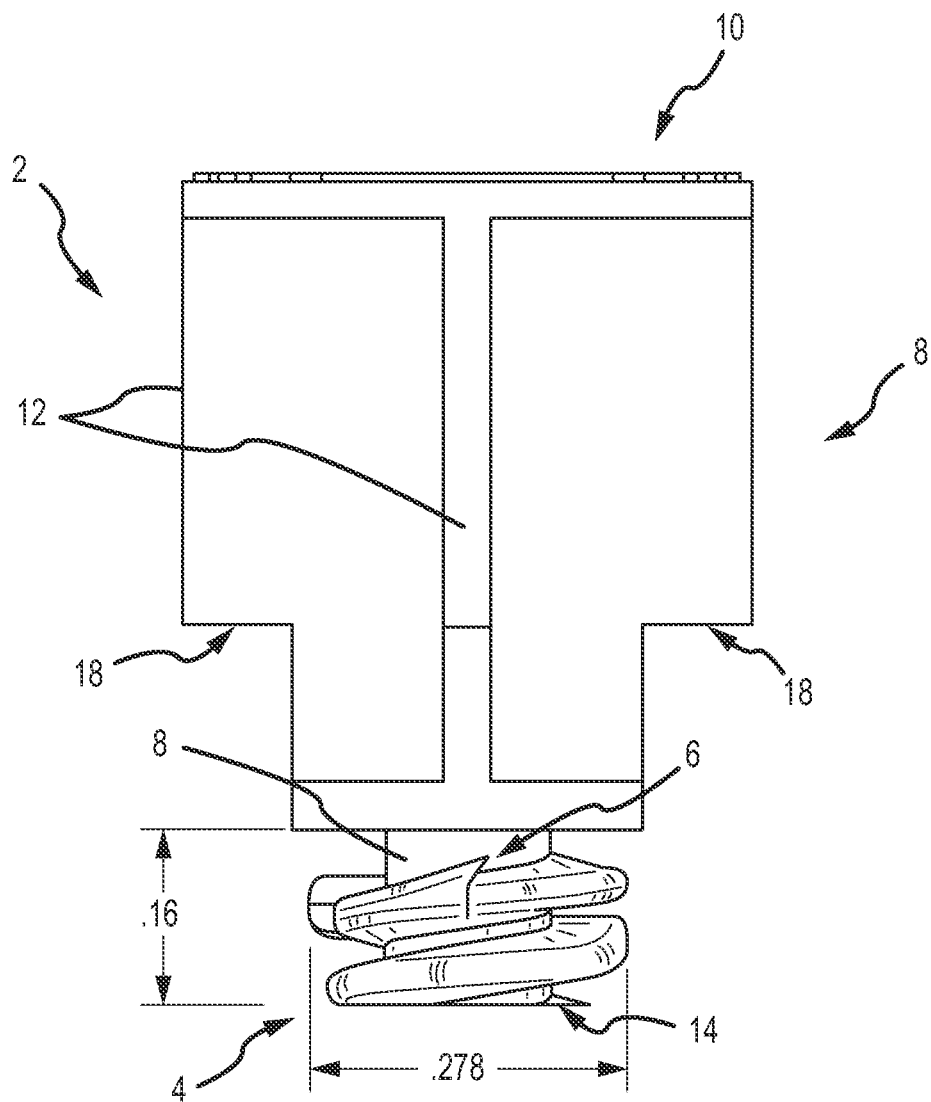
FIG. 3 is a front elevation view of the plunger according to the embodiment of FIG. 1.

FIG. 3 is a side elevation view of a plunger rod assembly 2 according to one embodiment. In various embodiments, the plunger rod assembly 2 comprises a threaded portion 4 having a length of between approximately 0.10 inches and 0.25 inches. In preferred embodiments, the length of the threaded portion 4 is between approximately 0.12 inches and 0.175 inches. In a preferred embodiment, the length of the threaded portion 4 is approximately 0.16 inches. In various embodiments, the threaded portion 4 comprises a maximum external width of between approximately 0.20 inches and approximately 0.50 inches. In preferred embodiments, the maximum width of the threaded portion 4 is between approximately 0.250 and 0.30 inches. In a preferred embodiment, the maximum width of the threaded portion 4 is approximately 0.278 inches.

The shaft portion 8 of the depicted embodiments comprises flange or shelf members 18 extending radially away from a center of the plunger rod shaft 8 and having a substantially flat surface for contacting a distal end of a syringe barrel and prevent translation of the shaft 8 past a predetermined point. The assembly 2 of the embodiment depicted in FIG. 3 is adapted for use with a mixing syringe, and typically the assembly 2 and any associated stopper is fully removed from a syringe prior to mixing and/or use. A secondary plunger rod (not shown) of longer length is then typically provided in the barrel to serve as the working plunger rod for the system. Embodiments of the present invention contemplate that the secondary plunger rod, and indeed any number or types of plunger rods may comprise features of the present invention including self-locking thread assemblies as shown and described herein.

In certain embodiments, the plunger rod assembly 2 comprises a plurality of locking elements 6 including, for example, barbs, projections, hooks, ramps, and similar features provided in the threads 14, the cylindrical portion 16, and/or a distal portion of the shaft portion 8. Although various embodiments depicted herein are provided with one locking element 6, embodiments of the present invention contemplate any number of locking elements, including two, three, four, five, or more.

Embodiments of the present invention are provided with external threads 14. The external threads 14 are adapted to communicate with female or internal threads of an aperture, recess, or similar feature of a stopper or piston. Alternatively, stoppers may be provided with an unthreaded aperture, and the device 2 of the present invention is provided wherein internal threads of the stopper are tapped or threaded by the external threads 14 of the plunger rod assembly 2.

Figure 4:
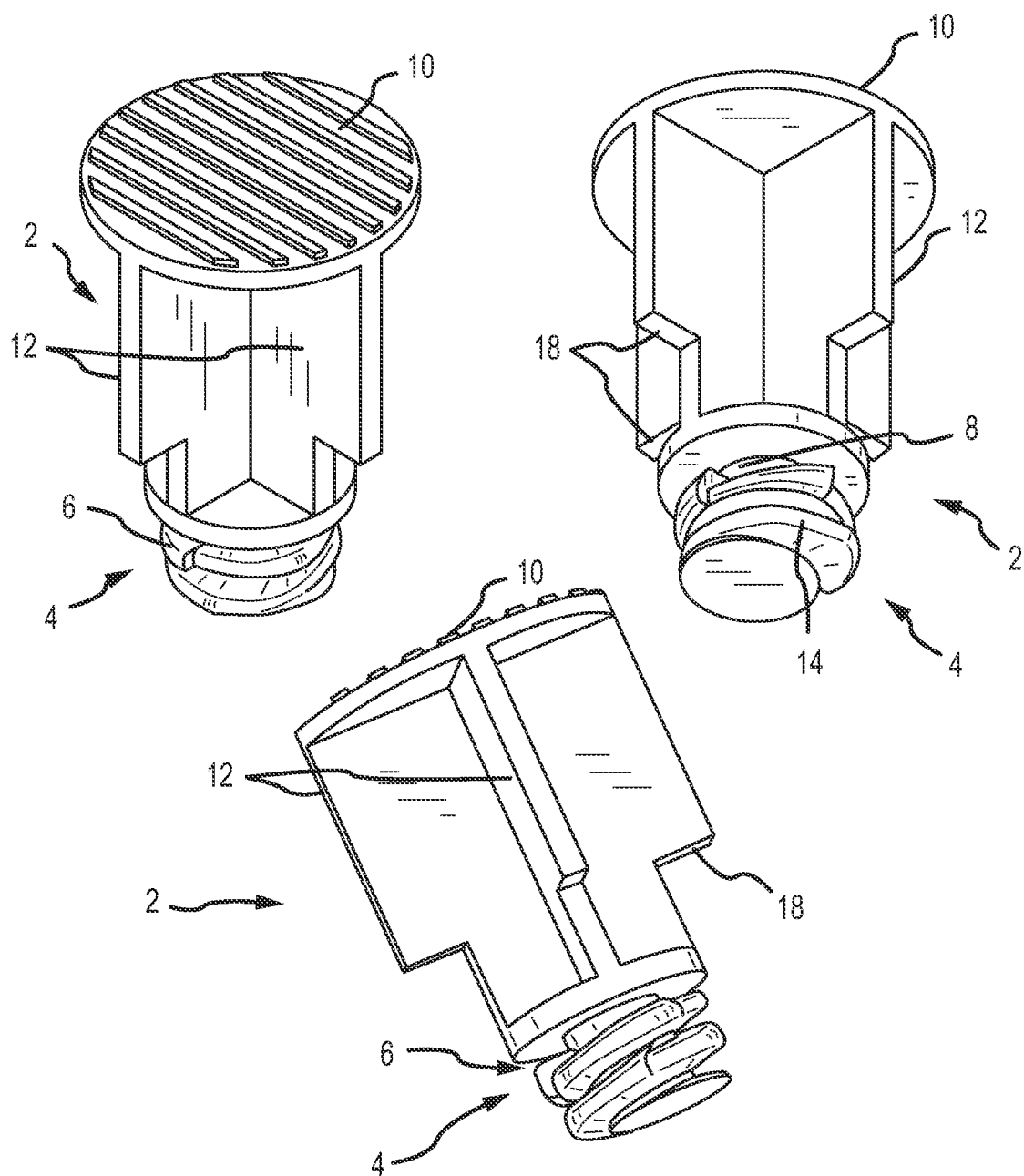
FIG. 4 provides various perspective views of the plunger according to the embodiment of FIG. 1.

FIG. 4 provides various perspective views of a plunger rod assembly 2 according to one embodiment of the present invention. Various features as shown and described herein are provided in FIG. 4. The details of FIG. 4 having been previously described, the perspective view of FIG. 4 are provided for additional illustration.

Figure 5:
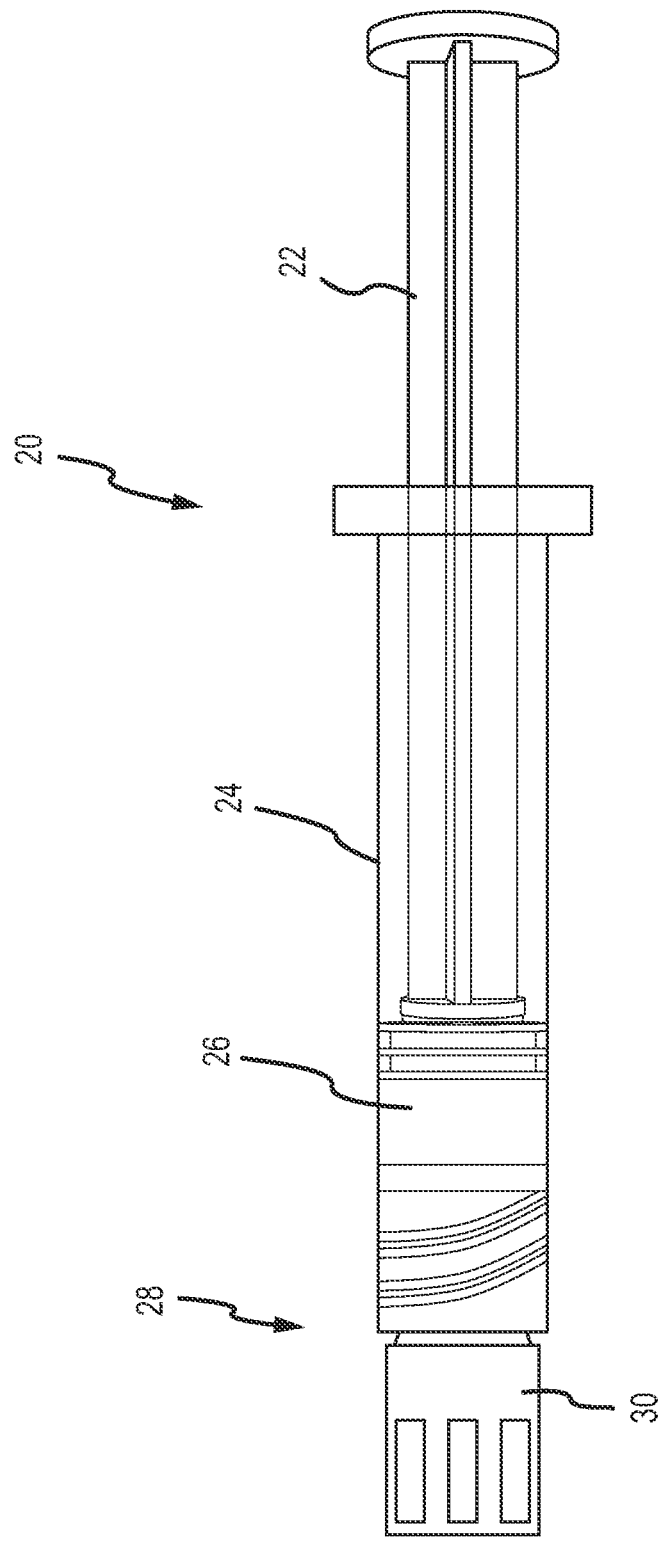
FIG. 5 is a perspective view of a plunger rod and syringe assembly according to one embodiment of the present invention.

FIG. 5 is a perspective view of one embodiment of the present invention. Although certain embodiments of the present invention are particularly well suited for use with temporary syringe barrel stoppers and associated plunger rods of shorter length, it will be expressly recognized that the present invention is not limited to such embodiments. For example, and as shown in FIG. 5, a syringe 20 is provided comprising a plunger rod 22 for driving a stopper 26 within a barrel 24 for dispensing syringe contents from a distal end 28 of the syringe. A cap or cover 30 is provided that is selectively removable from the syringe 20 prior to use. The plunger rod 22 of the depicted embodiment comprises a threaded feature on the distal end of the plunger rod 22 with locking features for securing the plunger rod 22 to the stopper 26. Such features, although not shown in FIG. 5, may comprise any one or more of the self-locking thread features as shown and described herein.

While various embodiments of the present invention have been described in detail, it is apparent that modifications and alterations of those embodiments will occur to those skilled in the art. However, it is to be expressly understood that such modifications and alterations are within the scope and spirit of the present invention. Further, the invention(s) described herein are capable of other embodiments and of being practiced or of being carried out in various ways. In addition, it is to be understood that the phraseology and terminology used herein is for the purposes of description and should not be regarded as limiting. The use of "including," "comprising," or "adding" and variations thereof herein are meant to encompass the items listed thereafter and equivalents thereof, as well as, additional items.

What is claimed is:

1. A plunger rod useful for supporting and sliding a stopper in a syringe barrel, the plunger rod comprising:
a first end and a second end;
the first end comprising a user-interface portion having a flange;
the second end comprising a threaded portion adapted for interconnection to a stopper;
wherein the threaded portion comprises a shaft having an external male thread and a predetermined thread geometry;
the external male thread comprising a locking element, wherein the locking element comprises a planar surface and a projection having a point, wherein the projection extends at an angle relative to the planar surface and terminates at the point, and wherein the locking element departs from a general path of the threaded portion, wherein the projection and the point extend over the external male thread, and wherein the external male thread provides enhanced pull-out resistance of the stopper; and
wherein the locking element comprises a deviation from the external male thread wherein a thread angle of the locking element is greater than a thread angle of the external male thread.

2. The plunger rod of claim 1, wherein the external male thread comprises at least 15 threads per inch.

3. The plunger rod of claim 1, wherein the external male thread comprises a thread pitch of between approximately 0.050 inches and 0.075 inches.

4. The plunger rod of claim 1, wherein the plunger rod is integrally formed with at least one resin selected from the group consisting of cyclic olefin resins, radiation-resistant polypropylenes, polypropylene, polycarbonates and polystyrene.

5. The plunger rod of claim 1, wherein the external male thread comprises a thread angle of between approximately 5.0 and 10.0 degrees and the locking element comprises a thread angle of between approximately 15.0 and 25.0 degrees.

6. The plunger rod of claim 1, wherein the locking element comprises a thread angle of between approximately 18.0 and 20.0 degrees.

7. The plunger rod of claim 1, wherein the external male thread comprises a thread angle of between approximately 7.0 and 8.0 degrees.

8. A plunger rod useful for supporting and sliding a stopper in a syringe barrel, the plunger rod comprising:
a first end and a second end;
the first end comprising a user-interface portion;
the second end comprising a threaded portion adapted for interconnection to a stopper;
wherein the threaded portion comprises an external male thread and a predetermined thread geometry having a first thread angle;
the external male thread comprising a locking element, wherein the locking element comprises a planar surface and at least one projection departing from a general path of the threaded portion, the projection comprising a second thread angle and terminating at a point and wherein the second thread angle is greater than the first thread angle;
wherein the projection and the point extend over a portion of the external male thread;
wherein the point is operable to extend at least partially into a stopper in an assembled state;
wherein the locking element permits threaded insertion of the external male thread into a stopper by rotation in a first direction and inhibits a reverse rotation, and wherein the external male thread provides enhanced pull-out resistance of the stopper, and wherein removal of the stopper from the plunger rod by rotation is inhibited by the locking element.

9. The plunger rod of claim 8, wherein said threaded portion comprises a thread pitch of between approximately 0.050 inches and 0.075 inches.

10. The plunger rod of claim 8, wherein the plunger rod comprises a length of between approximately 0.50 inches and 1.00 inches.

11. The plunger rod of claim 8, wherein the second thread angle comprises a thread angle of between approximately 18.0 and 20.0 degrees.

12. The plunger rod of claim 8, wherein the first thread angle comprises a thread angle of between approximately 7.0 and 8.0 degrees.

13. The plunger rod of claim 8, further comprising a stopper provided in force-transmitting communication with the external male thread.

14. The plunger rod of claim 13, further comprising a syringe having a barrel, and wherein the plunger rod and the stopper are provided within the barrel and comprise selectively removable elements relative to the syringe.

15. A syringe including a barrel, a plunger rod, and a stopper, the plunger rod comprising:
a first end and a second end;
the first end comprising a user-interface portion;
the second end comprising a threaded portion;

wherein the threaded portion comprises an external male thread and a predetermined thread geometry having a first thread angle;

a stopper connected to the second end of the plunger rod;

the external male thread comprising a locking element, wherein the locking element comprises a planar surface and at least one projection extending at an angle relative to the planar surface, and wherein the at least one projection departs from a general path of a pitch of the threaded portion, the projection comprising a second thread angle and a point, the projection and point extending over a portion of the external male thread;

wherein the second thread angle is greater than the first thread angle; and wherein the point extends at least partially into the stopper, the plunger rod provides enhanced pull-out resistance of the stopper, and a removal rotation of the plunger rod is operable to force the locking element further into the stopper.

16. The syringe of claim 15, wherein the plunger rod comprises right-handed threads operable to be inserted into the stopper by a clockwise rotation.

17. The syringe of claim 16, wherein the locking element opposes a counter-clockwise rotation and enables a clockwise rotation.

18. The syringe of claim 15, wherein the syringe comprises a pre-filled syringe.

19. The syringe of claim 18, wherein the syringe comprises leuprolide acetate.

* * * * *